(12) United States Patent
Petit (10) Patent No.: US 9,888,948 B2
(45) Date of Patent: Feb. 13, 2018

(54) DEVICE FOR GUIDING A SURGICAL INSTRUMENT INTO POSITION ON A BONE-ANCHOR ELEMENT INCLUDING A MEANS FOR REALIGNING A LINK ROD WITH THE ANCHOR ELEMENT, AND RELATED SYSTEM OF SURGICAL INSTRUMENTS

(71) Applicant: SAFE ORTHOPAEDICS, Eragny sur Oise (FR)

(72) Inventor: Dominique Petit, Verton (FR)

(73) Assignee: SAFE ORTHOPAEDICS, Eragny Sur Oise (FR)

( * ) Notice: Subject to any disclaimer, the term of this patent is extended or adjusted under 35 U.S.C. 154(b) by 0 days.

(21) Appl. No.: 14/415,212

(22) PCT Filed: Jul. 18, 2013

(86) PCT No.: PCT/FR2013/051741
§ 371 (c)(1),
(2) Date: Jan. 16, 2015

(87) PCT Pub. No.: WO2014/013203
PCT Pub. Date: Jan. 23, 2014

(65) Prior Publication Data
US 2015/0190183 A1 Jul. 9, 2015

(30) Foreign Application Priority Data
Jul. 19, 2012 (FR) ...................................... 12 57003

(51) Int. Cl.
*A61B 17/70* (2006.01)

(52) U.S. Cl.
CPC ...... *A61B 17/7083* (2013.01); *A61B 17/7086* (2013.01); *A61B 17/7091* (2013.01)

(58) Field of Classification Search
CPC ............ A61B 17/7086; A61B 17/7085; A61B 17/7083
See application file for complete search history.

(56) References Cited

U.S. PATENT DOCUMENTS 4,927,425 A * 5/1990 Lozier ................ A61B 17/7083
606/99
6,440,133 B1 8/2002 Beale et al.
(Continued)

FOREIGN PATENT DOCUMENTS

WO 2005099602 A2 10/2005
WO 2010054079 A2 5/2010
WO 2011080426 A2 7/2011

*Primary Examiner* — Ellen C Hammond
(74) *Attorney, Agent, or Firm* — Bachman & LaPointe, P.C.

(57) ABSTRACT

A device for guiding a surgical instrument having one end for coupling to the head of a bone anchor element and a longitudinal channel, the head of the bone anchor element having a tapped longitudinal recess intended for receiving a screw cap, said longitudinal recess leading into a transverse channel capable of receiving a link rod, characterized in that said guiding device includes a rod for guiding the surgical instrument, with a longitudinal axis A, having one end comprising two semi-tubular tabs in which the outer section matches the inner section of said longitudinal recess and in which the inner section is at least equal to the diameter of the link rod, the cross-section of the guiding device being always smaller than the section of the longitudinal channel of the surgical instrument in order to allow the insertion and the removal of said device in the distal direction.

9 Claims, 8 Drawing Sheets

(56) References Cited

U.S. PATENT DOCUMENTS

| | | | |
|---|---|---|---|
| 8,328,817 B2* | 12/2012 | Strauss | A61B 17/7032 606/102 |
| 8,747,409 B2* | 6/2014 | Ichelmann | A61B 17/7082 606/86 R |
| 9,216,043 B2* | 12/2015 | Stad | A61B 17/7076 |
| 2005/0010220 A1* | 1/2005 | Casutt | A61B 17/7008 606/86 A |
| 2005/0149048 A1* | 7/2005 | Leport | A61B 17/88 606/99 |
| 2006/0079909 A1 | 4/2006 | Runco et al. | |
| 2006/0247658 A1* | 11/2006 | Pond, Jr. | A61B 17/7091 606/104 |
| 2006/0264959 A1* | 11/2006 | Abdelgany | A61B 17/7083 606/86 R |
| 2009/0005814 A1* | 1/2009 | Miller | A61B 17/7037 606/246 |
| 2010/0114108 A1* | 5/2010 | Strauss | A61B 17/7032 606/102 |
| 2010/0160977 A1* | 6/2010 | Gephart | A61B 17/7035 606/305 |
| 2010/0331901 A1 | 12/2010 | Iott et al. | |
| 2011/0313464 A1 | 12/2011 | Mclean et al. | |
| 2012/0022594 A1* | 1/2012 | Walker | A61B 17/708 606/264 |
| 2012/0089191 A1* | 4/2012 | Altarac | A61B 17/025 606/279 |
| 2012/0143269 A1* | 6/2012 | Ichelmann | A61B 17/7082 606/86 R |
| 2013/0018418 A1* | 1/2013 | Petit | A61B 17/7076 606/246 |
| 2013/0030445 A1* | 1/2013 | Dauster | A61B 17/7076 606/104 |
| 2013/0245691 A1* | 9/2013 | Hutton | A61B 17/7032 606/278 |
| 2013/0296950 A1* | 11/2013 | Landry | A61B 17/1604 606/305 |
| 2014/0163625 A1* | 6/2014 | Meyer | A61B 17/7091 606/86 A |
| 2014/0249583 A1* | 9/2014 | Walker | A61B 17/708 606/279 |
| 2014/0277137 A1* | 9/2014 | Stad | A61B 17/7076 606/246 |

* cited by examiner

DEVICE FOR GUIDING A SURGICAL INSTRUMENT INTO POSITION ON A BONE-ANCHOR ELEMENT INCLUDING A MEANS FOR REALIGNING A LINK ROD WITH THE ANCHOR ELEMENT, AND RELATED SYSTEM OF SURGICAL INSTRUMENTS

BACKGROUND

Technical Field of the Invention

The invention relates to the field of surgery, specifically to the field of installing bone implants having a head provided such as to receive a screw cap and, where appropriate, an accessory such as a link rod.

The invention relates specifically to a device for guiding a surgical instrument into position on the head of a bone anchor element having a tapped longitudinal recess intended for receiving a screw cap, said longitudinal recess leading into a transverse channel capable of receiving a link rod, the surgical instrument having one end for coupling to the head of said bone anchor element and a longitudinal channel.

State of the Art

The placement of a link rod in a head of a bone anchor element remains a rather complicated operation, since the rod is often offset (in terms of height and/or laterally) relative to the head of the bone anchor element. It is thus sometimes necessary to resort to complementary instruments in order to place the link rod in said head of the anchor element.

An example of such an instrument is described in patent application WO2005/099602, which discloses a surgical instrument intended for pushing a link rod into a spinal implant.

Also known from U.S. Pat. No. 6,440,133 is a surgical instrument for reducing a rod into a bone anchor element. The instrument includes an element that engages with the bone anchor element, said engaging element having a distal portion suitable for receiving a portion of the link rod, a reducing element arranged in a mobile fashion about the element engaging the bone anchor element and an actuator pivotably coupled with the element engaging the bone anchor element and pivotably coupled to the reducing element, the actuator making it possible to move the reducing element such that the latter comes into contact with the link rod and to move the latter towards the bone anchor element. The element engaging the bone anchor element includes a pair of flexible arms and a tab on the distal end of each of the flexible arms, each of said tabs defining a channel for receiving the link rod inside thereof.

However, said instruments each have a major defect which is the positioning on the head of the anchor element. Indeed, accurate positioning is necessary in order to ensure correct attachment between the instrument and the anchor element, which requires a careful gesture. The tissues surrounding the surgical incision actually impede access to the head of the anchor element and sometimes make it impossible to install these instruments given the constitution thereof. Placement is made even more difficult by the fact that the heads of the anchor elements used are mobile most of the time.

SUMMARY

The invention aims to solve these problems by providing an instrument that makes it possible to guide a guiding device while ensuring the positioning of the link rod relative to the head of the bone anchor element, whether the head of a stationary or multiaxial element head.

The invention also relates to providing a guiding device that facilitates the installation of the surgical instrument on the head of the bone anchor element.

The invention, in the broadest sense thereof, relates to a device for guiding a surgical instrument having one end for coupling to the head of a bone anchor element and a longitudinal channel, the head of the bone anchor element having a tapped longitudinal recess intended for receiving a screw cap, said longitudinal recess leading into a transverse channel capable of receiving a link rod, characterised in that said guiding device includes a rod for guiding the surgical instrument, with a longitudinal axis A, having one end comprising two semi-tubular tabs in which the outer section matches the inner section of said longitudinal recess and in which the inner section is at least equal to the diameter of the link rod, the cross-section of the guiding device being always smaller than the section of the longitudinal channel of the surgical instrument in order to enable the insertion and the removal of said device in distal direction.

The guiding device thus arranged makes it possible to guide the surgical instrument on the head of the bone anchor element but also to realign the link rod longitudinally with the head of the anchor element.

When the head of the element is mobile, the guiding device makes it possible to position the head in a position in which the tissues surrounding the incision do not impede the surgical deed.

Said tabs advantageously have a cross-section that fits into the space defined between the tapped inner wall of said longitudinal recess, and the plane parallel to the median longitudinal plane, crossing the surface of the link rod when the latter is positioned in said transverse channel.

The inner section of the semi-tubular tabs is preferably arranged such as to allow longitudinal positioning of the rod when the device is inserted in the longitudinal recess. According to a specific embodiment, the semi-tubular tabs are extended at the distal portion by an area for longitudinal positioning of the link rod when the guiding device is placed in the head of the bone anchor element, said area comprising a transverse channel having an inner section at least equal to the diameter of the link rod.

According to a specific embodiment, the inner section of the semi-tubular tabs comprises a widened area extending beyond the longitudinal recess when the device is inserted in said recess. Said widened area ensures a lateral clearance of the link rod, which facilitates the surgical deed by not requiring a perfectly aligned position between the link rod and the head of the anchor element.

The outer section of the semi-tubular tabs advantageously comprises a shoulder arranged such as to abut with the head of the anchor element. This provides a visual and tactile indication of the correct placement of the guiding device in the head of the bone anchor element.

According to a specific embodiment, the semi-tubular tabs are extended in the distal direction by a conical area capable of causing the separation of the flexible proximal end of a surgical instrument inside of which said guiding device is inserted.

According to another embodiment, the semi-tubular tabs are flexible and flared when inactive. This makes it possible to provide a function of snap-fitting the guiding device onto the head of the bone anchor element, and thus temporary holding of the latter on said head.

The invention also relates to a system of surgical instruments including a surgical instrument having one end for coupling to the head of a bone anchor element and a longitudinal channel, the head of the bone anchor element having a tapped longitudinal recess intended for receiving a screw cap, said longitudinal recess leading into a transverse channel capable of receiving a link rod, characterised by also including a rod for guiding the surgical instrument, with a longitudinal axis A, having one end comprising two semi-tubular tabs in which the outer section matches the inner section of said longitudinal recess and in which the inner section is at least equal to the diameter of the link rod, the cross-section of the guiding device being always smaller than the section of the longitudinal channel of the surgical instrument in order to enable the insertion and the removal of said device in distal direction.

Said surgical instrument advantageously has, at the end thereof, two arms each having a shoulder extending transversely over the inner surface of the arm, said shoulder being capable of fastening to a matching recess provided on the head of the bone anchor element.

According to a specific embodiment, said arms of the instrument are flexible, and said device has a frusto-conical area capable of causing the separation of said flexible arms when the guiding device is inserted into said surgical instrument. This therefore facilitates the placement of the surgical instrument on the head of the bone anchor element.

According to another advantageous embodiment, the guiding device and the surgical instrument are made at least partially by polymer injection for single use.

The guiding device is intended to be supplied as part of a kit of instruments described in application WO2011/080426.

BRIEF DESCRIPTION OF THE DRAWINGS

Further objectives and advantages of the invention will become apparent from the following description made in reference to the appended drawings, wherein.

DETAILED DESCRIPTION

In relation to FIGS. 1 to 7, the invention describes a device 1 for guiding a surgical instrument 5 on a bone anchor element 2 according to a first embodiment, said instrument 5 having one end 50 for coupling to the head 3 of the bone anchor element 2 and a connecting longitudinal channel 51.

Figure 1:
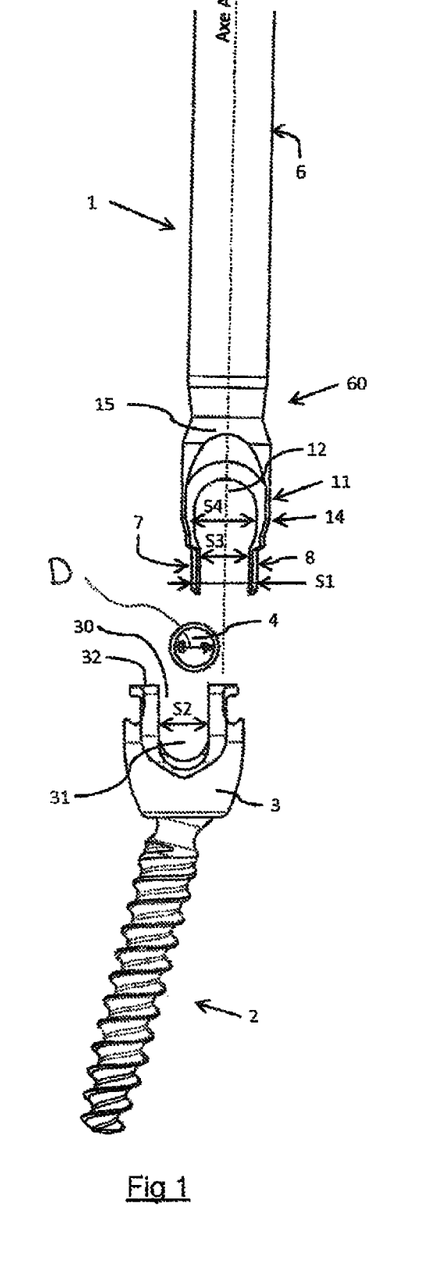
FIG. 1 is a view of the guiding device according to a first invention and a bone anchor element.

In the implemented embodiment, the head 3 of the bone anchor element 2 has a tapped longitudinal recess 30 intended for receiving a cap which can be screwed (not shown). The head 3 of the bone anchor element 2 also comprises a transverse channel 31 leading into the longitudinal recess 30, said transverse channel 31 being capable of receiving a link rod 4.

In the described embodiment, the guiding device 1 includes a guiding rod 6, with a longitudinal axis A, intended for guiding the surgical instrument 5 when placed on the head 3 of the bone anchor element 2, and two semi-tubular tabs 7, 8 arranged at one of the ends 60 of the guiding rod 6.

The two semi-tubular tabs 7, 8 are shaped such as to have an outer section S1 that matches the inner section S2 of the longitudinal recess of a part and an inner section S3 at least equal to the diameter D of the link rod 4. Furthermore, as will be explained hereinafter, the guiding device 1 is configured such as to have a cross-section that is always smaller than the section of the longitudinal channel 51 of the surgical instrument 5 in order to allow the insertion and the removal of the guiding device 1 in the distal direction.

The term "distal" is understood to refer to the portion or the end of an element that is furthest from the bone anchor element 2, while the term "proximal" is understood to refer to the portion or end of the element that is closest to the bone anchor element 2.

Figure 3:
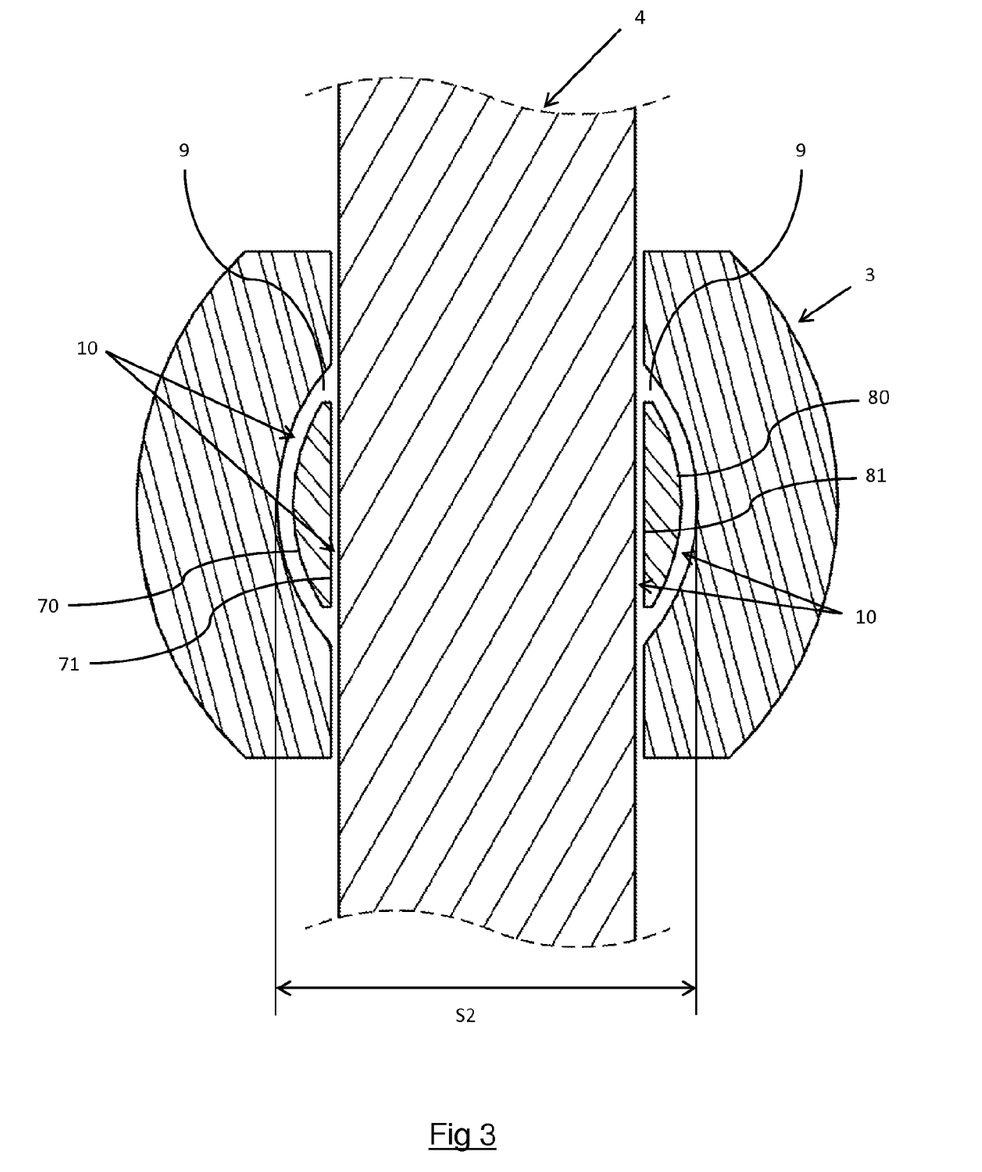
FIG. 3 is a section view along the axis of the guiding device of FIG. 2.

Advantageously, the semi-tubular tabs 7, 8 have a cross-section that fits into the space defined between the tapped inner surface of the longitudinal recess 30 and the plane parallel to the median longitudinal plane, crossing the surface of the link rod 4 when the latter is positioned in the transverse channel 31 (FIG. 3).

In order to facilitate the removal of the guiding device 1 once the surgical instrument 5 is in place on the head 3 of the bone anchor element 2, it has been provided to size the semi-tubular tabs 7, 8 such as to leave a slight clearance 10 between the tabs 7, 8 and the inner surface of the longitudinal recess 30 and between the tabs 7, 8 and the surface of the link rod 4. For this purpose, according to a preferred configuration, the semi-tubular tabs 7, 8 have a distance of 5.5 millimeters measured between the respective inner surfaces thereof (standard diameter of the rods) and a distance of 7.5 millimeters measured between the outer surfaces thereof. The semi-tubular tabs 7, 8 are obviously not limited to these dimensions, which may be revised according to the dimensions of the link rods and the rods of the bone anchor elements used.

In the example shown in FIG. 3, the outer surface 70, 80 of the semi-tubular tabs 7, 8 is rounded, while the inner surface 71, 81 thereof is planar. According to an alternative embodiment, it can also be provided for the inner surface of the tabs to have a concave shape, the tabs thus having a profile with a semi-circular section.

Figure 2:
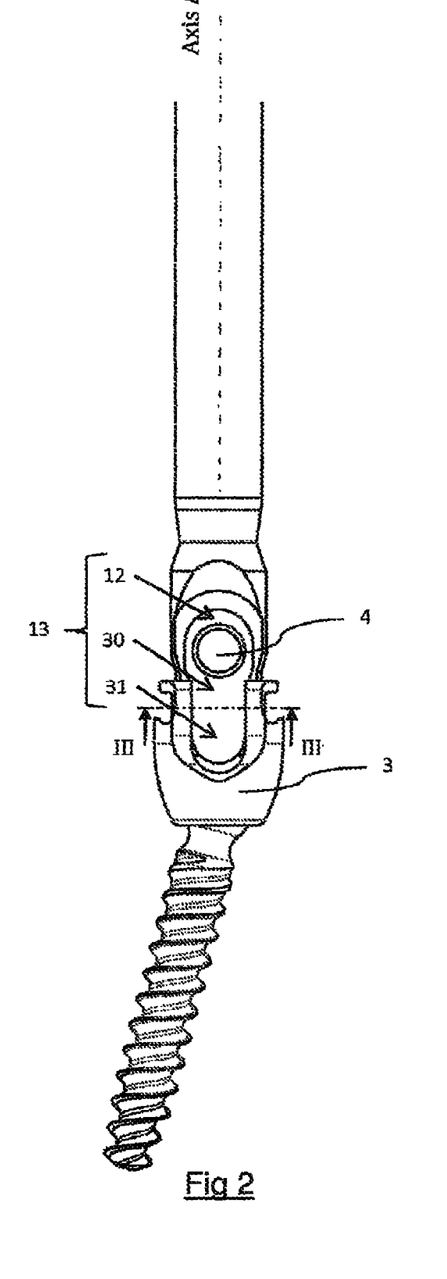
FIG. 2 shows the guiding device in position on the bone anchor element.

The semi-tubular tabs 7, 8 are advantageously extended at the distal portion thereof by an area for longitudinal positioning 11 of the rod when mounting the guiding device 1 on the head 3 of the bone anchor element 2. The longitudinal positioning of the link rod 4 is defined relative to the axis A of the latter. The longitudinal positioning area 11 comprises a transverse channel 12 having an inner section S4 at least equal to the diameter of the link rod 4. The transverse channel 12 of the longitudinal positioning area 1 is such that when the guiding device 1 is mounted on the head 3 of the bone anchor element 2, the semi-tubular tabs 7, 8 and the positioning area 11 define with the head 3 of the bone anchor element 2 an oblong slot 13 extending according to the longitudinal axis A (FIG. 2).

The positioning area 11 advantageously has an inner section S4 that is larger than the diameter D of the link rod 4. This widening of the section with regard to that of the semi-tubular tabs 7, 8 has the advantage of allowing a lateral clearance of the link rod 4 and thus of limiting the force to be applied to said rod 4 in order possibly to reposition same aligned with the transverse channel 31 during the placement of the guiding device 1 in the head 3 of the bone anchor element 2.

The outer section S1 of the semi-tubular tabs 7, 8 advantageously comprises a shoulder 14 arranged such as to abut with the upper surface 32 of the head 3 of the bone anchor element 3. The term "upper" is defined herein relative to the position of the bone anchor element 2 in the figures. In the example shown, the shoulder 14 defines the semi-tubular tabs 7, 8 of the longitudinal positioning area 11 of the rod. Thus, as shown in FIG. 2, the positioning area 11 extends beyond the longitudinal recess 30 of the bone anchor element 2 when the guiding device 1 is mounted in the head 3 of the bone anchor element 2.

According to another embodiment, it can be provided for the shoulder to abut with a chamfer made at the entrance of the longitudinal recess 30 of the head 3 of the bone anchor element 2.

According to a specific configuration, the semi-tubular tabs 7, 8 are flexible and flared when inactive. This has the advantage of making it possible to retain the guiding device 1 once the latter is in position in the head 3 of the bone anchor element 2, this embodiment lacking the previously described clearance 10.

The semi-tubular tabs 7, 8 are advantageously connected together by a joining portion 15 to which the guiding rod 6 is secured. In the example shown in FIG. 4, the guiding rod 6 is secured to the joining portion 15 of the semi-tubular tabs 7, 8 by means of a part forming a tenon 16 arranged on the joining portion 15 and a portion forming a mortice 17 formed at the end 60 of the guiding rod 6. Advantageously, the portions that form the tenon and mortice 16, 17 are configured such that the guiding rod 6 and the semi-tubular tabs 7, 8 are assembled by force. In order to reinforce the securing of the guiding rod 6 to the semi-tubular tabs 7, 8, it is possible to glue all or part of the portions forming the tenon and mortice 16, 17.

Figure 4:
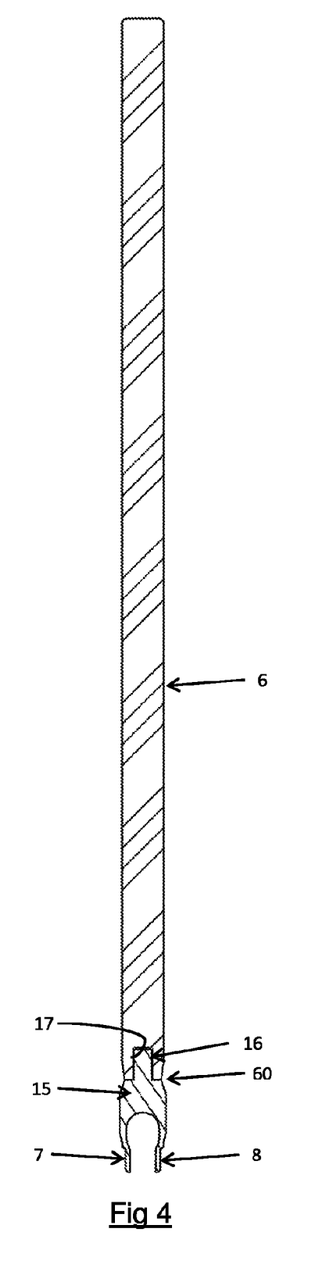
FIG. 4 is a longitudinal section view of the guiding device according to the invention.

Advantageously, the portion forming a tenon 16 of the joining portion 15 comprises flattened areas capable of engaging with flattened areas arranged on the inner surface of the portion forming a mortice 17 of the guiding rod 6. This arrangement has the advantage of preventing the rotation of the semi-tubular tabs 7, 8 relative to the guiding rod 6.

The assembly is such that once assembled the two elements cannot be taken apart.

It is obvious that the two elements can be assembled by any means known to a person skilled in the art without departing from the framework of the invention.

Figure 5:
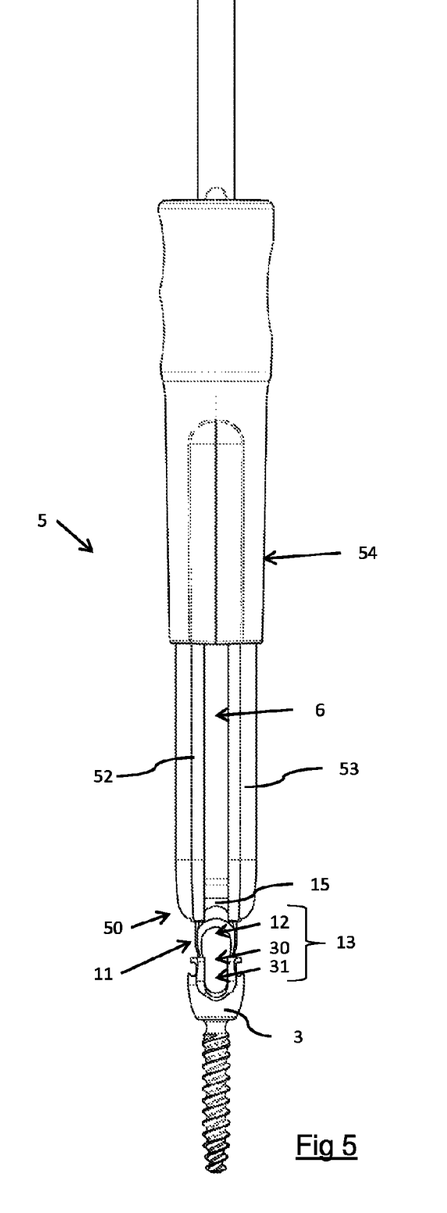
FIGS. 5 to 7 show the placement and removal of the surgical instrument on the bone anchor element.
Figure 6:
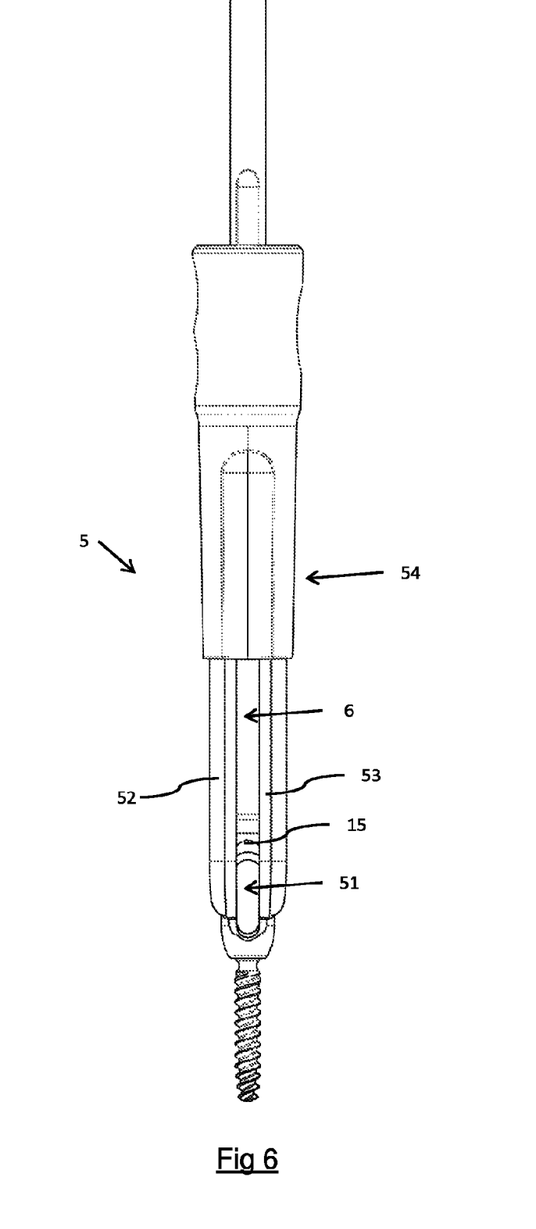
Figure 7:
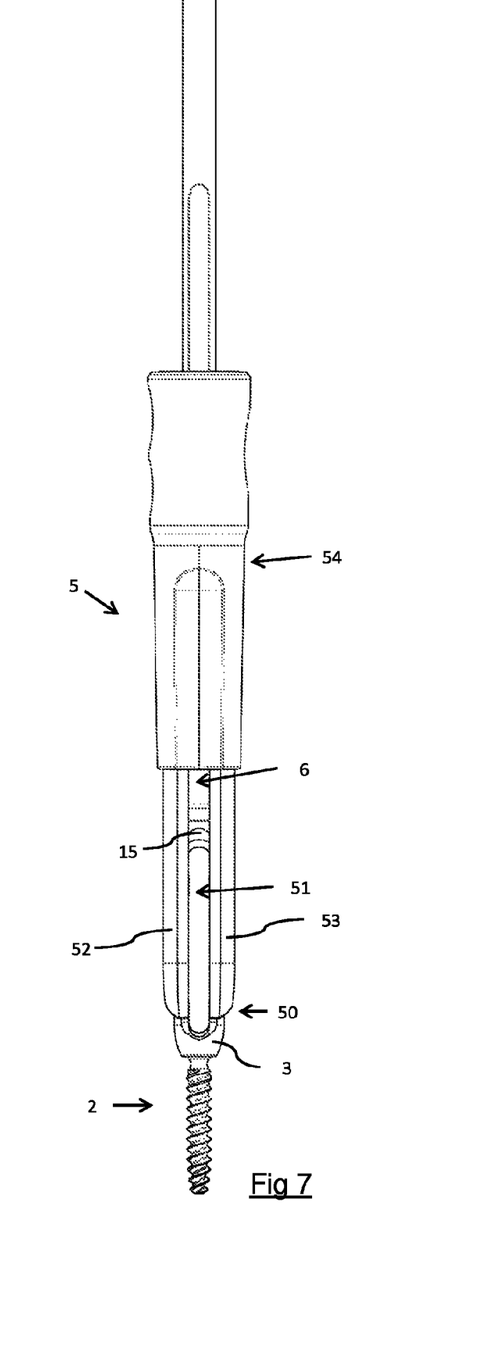

FIGS. 5 to 7 show the steps of placing a surgical instrument 5, provided in the form of a tube, on the bone anchor element 2 (FIGS. 5 and 6) and then of removing the guiding device 1 once the surgical instrument 5 is in position on the head 3 of the bone anchor element 2 (FIG. 7). In the example shown, the surgical instrument 5 comprises two flexible arms 52, 53 connected to one another at the distal portion by means of a sleeve 54 and arranged relative to one another in order to define a longitudinal channel 51 connecting on either side of the ends of the instrument 5, said channel being capable of receiving the guiding rod 6 of the guiding device 1. Each arm 52, 53 has a shoulder or any equivalent element (pin, lug, etc.) extending transversely towards the longitudinal channel 51, said shoulder being capable of being fastened in a recess or cavity with a matching shape provided on the head 3 of the bone anchor element 2.

Figure 8:
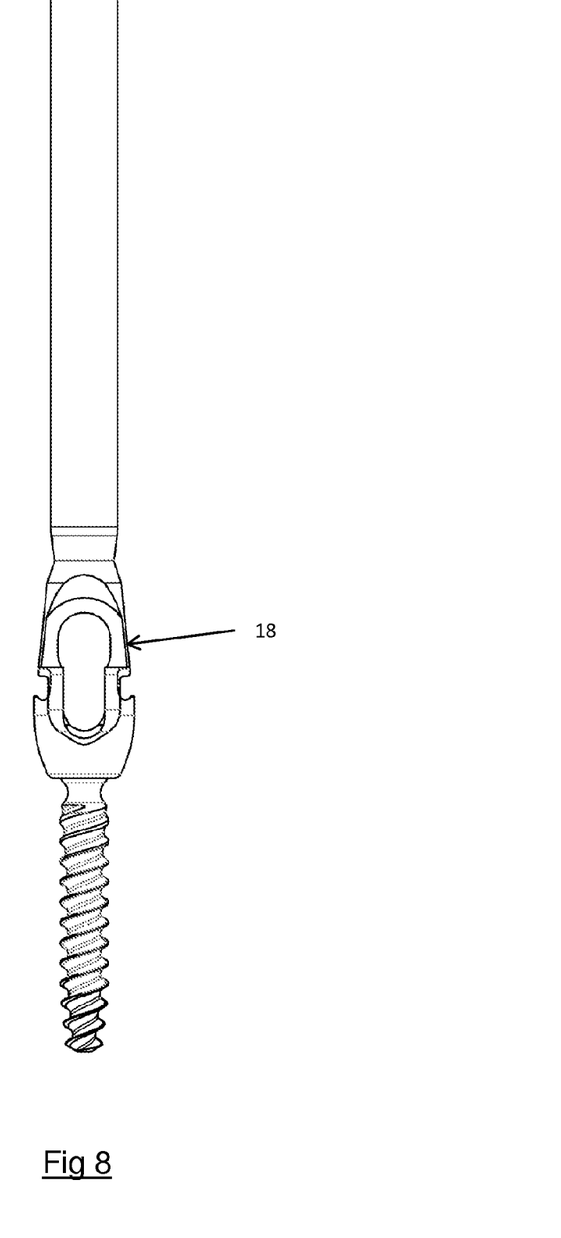
FIG. 8 shows the guiding device according to another embodiment of the invention, said guiding device being ready to be positioned on the bone anchor element.

In order to facilitate the placement of the surgical instrument 5, according to another embodiment shown in FIG. 8, a guiding device 1 may be provided in which the semi-tubular tabs 7, 8 are extended in the distal direction by a frusto-conical area 18. The frusto-conical area 18 is arranged such as to be flared in the proximal direction. This conical area 18 causes the separation of the flexible proximal area of the surgical instrument 5 into which said guiding device 1 is inserted when the surgical instrument 5 passes over the conical area 18.

The cone advantageously has a base with a section larger than the outer section of the arms of the surgical instrument 5. Thus, when the arms are slid along the guiding rod 6, the frusto-conical area 18 gradually separates the arms 52, 53 of the surgical instrument 5. The slightly separated position of the arms 52, 53 of the surgical instrument 5 thus obtained when said instrument reaches the position for snap-fitting onto the head 3 of the bone anchor element 2 facilitates the snap-fitting of said arms 52, 53 onto the head 3 of the bone anchor element 2.

The guiding device 1 and the surgical instrument are advantageously made at least partially by polymer injection for single use.

In the preceding embodiment, the guiding device 1 according to the invention includes two separate elements: a first element made up of the guiding rod 6 and a second element made up of the semi-tubular tabs 7, 8. In this embodiment, the guiding rod 6 is advantageously made of a polymer, while the semi-tubular tabs 7, 8 are made of metal.

The invention may, however, provide for a guiding device 1 in which the guiding rod 6 and the semi-tubular tabs 7, 8 are formed integrally without thereby departing from the framework of the invention.

The invention is described above as an example. It is understood that those skilled in the art are capable of creating different alternative embodiments of the invention without departing from the framework of the invention.

The invention claimed is:

1. A system of surgical instruments comprising:
   a bone anchor element comprising a head having a tapped longitudinal recess configured to receive a screw cap, said longitudinal recess leading into a transverse channel configured to receive a link rod,
   a surgical instrument having one end for coupling to the head of the bone anchor element and a longitudinal channel,
   a guiding device for the surgical instrument for placement onto the head of the bone anchor element, said guiding device comprising a rod for guiding the surgical instrument, with a longitudinal axis, having one end comprising two semi-tubular tabs arranged with each other to define an outer section matching the inner section of said longitudinal recess and an inner section being at least equal to the diameter of the link rod, the cross-section of the guiding device being always smaller than a section of the longitudinal channel of the surgical instrument in order to allow the insertion of the surgical instrument onto the guiding device and the removal of said guiding device in the distal direction once the surgical instrument is placed on the head of the bone anchor element.

2. The system of surgical instruments according to claim 1, wherein the semi-tubular tabs have a cross-section that fits into a space defined between a tapped inner wall of said tapped longitudinal recess and an outer surface of the link rod when the latter is positioned in said transverse channel.

3. The system of surgical instruments according to claim 1, wherein the semi-tubular tabs are placed in front of a part for longitudinal positioning of the link rod when the guiding device is placed in the head of the bone anchor element, said part comprising a transverse channel having an inner section at least equal to the diameter of the link rod.

4. The system of surgical instruments according to claim 1, wherein the inner section of the semi-tubular tabs comprises a widened area extending out of the longitudinal recess when the device is placed in said recess.

5. The system of surgical instruments according to claim 1, wherein the outer section of the semi-tubular tabs comprises a shoulder configured to abut with the head of the anchor element.

6. The system of surgical instruments according to claim 1, wherein said guiding device comprises a conical portion preceding the semi-tubular tabs, said conical portion being configured to separate the end of the surgical instrument inside of which said guiding device is inserted, said end being flexible.

7. The system of surgical instruments according to claim 1, wherein the semi-tubular tabs are flexible and flared when inactive.

8. The system of surgical instruments according to claim 1, wherein said surgical instrument has, at the end thereof, two flexible arms, said guiding device having a frusto-conical area configured to separate said flexible arms when the guiding device is inserted into said surgical instrument.

9. The system of surgical instruments according to claim 1, wherein the guiding device and the surgical instrument are made at least partially by polymer injection for single use.

* * * * *